(12) United States Patent
Boss et al.

(10) Patent No.: US 7,981,694 B2
(45) Date of Patent: Jul. 19, 2011

(54) SOLID PHASE ISOLATION OF PROTEINS, NUCLEIC ACIDS AND OTHER MACROMOLECULES

(75) Inventors: Gerry R. Boss, La Jolla, CA (US); Stephen B. Jones, San Diego, CA (US); Jeffrey C. Chen, San Gabriel, CA (US); Friederike von Lintig, San Diego, CA (US); Stephanie Hoffman, Patatuma, CA (US); Adam Kimmerly, San Diego, CA (US); Joann Luu, San Jose, CA (US); Matthew Christopher Mycroft, Sierra Madre, CA (US)

(73) Assignee: The Regents of the University of California, Oakland, CA (US)

( * ) Notice: Subject to any disclaimer, the term of this patent is extended or adjusted under 35 U.S.C. 154(b) by 1556 days.

(21) Appl. No.: 10/767,251

(22) Filed: Jan. 28, 2004

(65) Prior Publication Data
US 2005/0164408 A1    Jul. 28, 2005

Related U.S. Application Data

(60) Provisional application No. 60/443,231, filed on Jan. 28, 2003.

(51) Int. Cl.
*G01N 33/543* (2006.01)
(52) U.S. Cl. ........ 436/518; 436/524; 436/527; 436/528; 436/532
(58) Field of Classification Search .................. 436/518, 436/524, 527, 528, 532; 435/7.1, 283.1
See application file for complete search history.

(56) References Cited

U.S. PATENT DOCUMENTS

| | | | | |
|---|---|---|---|---|
| 4,251,616 A * | 2/1981 | Hendriks | .................. | 430/108.4 |
| 4,366,242 A * | 12/1982 | Neumann et al. | ............... | 435/7.4 |
| 4,965,087 A * | 10/1990 | Wolfbeis et al. | ............. | 427/2.11 |
| 5,296,347 A * | 3/1994 | LaMotte, III | .................... | 435/5 |
| 5,470,609 A * | 11/1995 | Leach et al. | .................. | 427/140 |
| 5,599,668 A * | 2/1997 | Stimpson et al. | ................. | 435/6 |
| 5,741,635 A | 4/1998 | Boss | | |
| 6,156,550 A * | 12/2000 | Glad | ............................ | 435/180 |
| 6,294,401 B1 * | 9/2001 | Jacobson et al. | ................ | 438/99 |
| 6,569,619 B1 * | 5/2003 | Sivaraja | ............................ | 435/6 |
| 6,699,677 B1 * | 3/2004 | Schall et al. | ................. | 435/7.24 |

(Continued)

FOREIGN PATENT DOCUMENTS

WO    WO 98/56806 A1    12/1998

OTHER PUBLICATIONS

"Affinity Chromatography," from http:mobitec.de. Publication date unknown, 4 pages.

(Continued)

*Primary Examiner* — Melanie Yu
(74) *Attorney, Agent, or Firm* — Fenwick & West LLP (57) ABSTRACT

The invention is a method for the isolation of molecules of interest using tubes in which at least a portion of the inner walls of the tube are coated with microbeads that are coated with a capture reagent to bind the molecule of interest. The microbeads may be glass or polymer beads. The invention is a method and apparatus for preparation of the tubes for use in the method of the invention. The invention is a method for determining ratios of guanine nucleotides bound to guanine-nucleotide binding proteins.

24 Claims, 3 Drawing Sheets

U.S. PATENT DOCUMENTS

| | | | | |
|---|---|---|---|---|
| 2003/0046717 | A1* | 3/2003 | Zhang | 800/8 |
| 2003/0068616 | A1* | 4/2003 | Polansky | 435/5 |
| 2003/0153010 | A1* | 8/2003 | Orth et al. | 435/7.5 |
| 2004/0014101 | A1* | 1/2004 | Liu et al. | 435/6 |

OTHER PUBLICATIONS

Albarghouthi, M. et al., "Immobilization of Antibodies on Alginate-Chitosan Beads," International Journal of Pharmaceutics, 2000, pp. 23-34, vol. 206.

"Attach a Protein Onto Glass, Silica, or Quartz Surface Using a Cleavable Cross-Linker," Technical Resource, Pierce Biotechnology, Oct. 2002, 7 pages.

Chen et al., High-Efficiency Solid-Phase Capture Using Glass Beads Bonded to Microcentrifuge Tubes: Immnoprecipitation of Proteins from Cell Extracts and Assessment of Ras Activation, Analytical Biochemistry, 2002, pp. 298-304, vol. 302.

"CNBr-activated Sepharose 4B," Amersham Biosciences, 2002, 12 pages.

"Cross-linking," Pierce Biotechnology, 2002, [Online] [Retrieved on Jan. 9, 2004] Retrieved from the Internet<URL:http://www.piercenet.com/Objects/View.cfm?type=Page&ID=70485B9B-2585-45C7-846B>.

Denizli, A. et al., "Protein A Immobilized Polyhydroxyethylmethylacrylate Beads for Affinity Sorption of Human Immunoglobulin G," Journal of Chromatography B, 1995, pp. 13-19, vol. 668.

"Double Agents Cross-linking Reagents Selection Guide," Pierce Biotechnology, 2003, 32 pages.

"EDC," Instructions, Pierce Biotechnology, May 2002, 3 pages.

Fahrner, R.L. et al., "Performance Comparison of Protein A Affinity-Chromatography Sorbents for Purifying Recombinant Monoclonal Antibodies," Biotechnol. Appl. Biochem., 1999, pp. 121-128, vol. 30.

Hale, J.E. et al., Purification of Humanized Murine and Murine Monoclonal Antibodies Using Immobilized Metal-Affinity Chromatography, Analytical Biochemistry, 1994, pp. 29-33, vol. 222.

Hammerl, P. et al., "Particulate Nitrocellulose as a Solid Phase for Protein Immobilization in Immuno-Affinity Chromatography," Journal of Immunological Methods, 1993, pp. 59-66, vol. 165.

Kim, J. et al., "Protein Immobilization on Plasma-Polymerized Ethylenediamine-Coated Glass Slides," Analytical Biochemistry, 2003, pp. 41-45, vol. 313.

Krogh, T.N. et al., "Protein Analysis Using Enzymes Immobilized to Paramagnetic Beads," 1999, pp. 153-162, vol. 274.

Leibl, H. et al., "Separation of Polysaccharide-Specific Human Immunoglobulin G Subclasses Using a Protein A Superose Column with a pH Gradient Elution System," Journal of Chromatography, 1996, pp. 51-56, vol. 639.

Nisnevitch, M. et al., "The Solid Phase in Affinity Chromatography Strategies for Antibody Attachment," J. Biochem. Biophys. Methods, 2001, pp. 467-480, vol. 49.

Phillips, T.M. et al., "Isolation and Quantitation of Serum IgE Levels by High Performance Immunoaffinity Chromatography," Journal of Chromatography, 1985, pp. 205-211, vol. 327.

Phillips, T.M., "Multi-Analyte Analysis of Biological Fluids with a Recycling Immunoaffinity Column Array," J. Biochem. Biophys. Methods, 2001, pp. 253-262, vol. 49.

Phillips, T.M. et al., "Protein A-Coated Glass Beads: Universal Support Meduim for High-Performance Immunoaffinity Chromatography," Journal of Chromatography, 1985, pp. 213-219, vol. 327.

Quitadamo, I.J. et al., "Efficient Purification of Mouse Anti-FGF Receptor IgM Monclonal Antibody by Magnetic Beads," Hybridoma, 1998, pp. 199-207, vol. 17, No. 2.

Scheele, J.S. et al., "Determination of Absolute Amounts of GDP and GTP Bound to Ras in Mammalian Cells: Comparison of Parental and Ras-Overproducing NIH 3T3 Fibroblasts," Proc. Natl. Acad. Sci. USA, Cell Biology, Feb. 1995, pp. 1097-1100, vol. 92.

Schneider, C. et al., "A One-Step Purification of Membrane Protein Using a High Efficiency Immunomatrix," The Journal of Biological Chemistry, Sep. 25, 1982, pp. 10766-10769, vol. 257, No. 18.

Walsh, M.K. et al., "Optimizing the Immobilization of Single Stranded DNA onto Glass Beads," J Biochem Biophys. Methods, 2001, pp. 221-231, vol. 47.

Bos, J.L., "ras-Oncogenes in Human Cancer: a Review," Cancer Research, 1989, pp. 4682-4689, vol. 49.

Bradford, M.M., "A Rapid and Sensitive Method for the Quantitation of Microgram Quantities of Protein Utilizing the Principle of Protein Dye Binding," Analytical Biochemistry, 1976, pp. 248-254, vol. 72.

Brunk, C. et al., "Assay for Nanogram Quantities of DNA in Cellular Homogenates," Analytical Biochemistry, 1979, pp. 497-500, vol. 92.

Dupuy, A.J., et al., "Activation of the Rap1 Guanine Nucleotide Exchange Gene, CalDAG-GEF I, in BXH-2 Murine Myeloid Leukemia," The Journal of Biological Chemistry, Apr. 13, 2001, pp. 11804-11811, vol. 276, No. 15.

Gibbs, J.B. et al., "Identification of Guanine Nucleotides Bound to ras-Encoded Proteins in Growing Yeast Cells," The Journal of Biological Chemistry, Aug. 5, 1987, pp. 10426-10429, vol. 262, No. 22.

Guha, A. et al., "Proliferation of Human Malignant Astrocytomas is Dependent on Ras Activation," Oncogene, 1997, pp. 2755-2765, vol. 15.

Hall, A., "Rho GTPases and the Actin Cytoskeleton," Science, 1998, pp. 509-514, vol. 279.

Mul, F.P.J. et al., "An Improved Method for the Purification of Basophilic Granulocytes from Human Blood," Journal of Immunological Methods, 1992, pp. 207-214, vol. 149.

Müller-Schulte, D. et al., "Novel Magnetic Micro Spheres on the Basis of Poly(vinylalcohol) as Affinity Medium for Quantitative Detection of Glycated Haemoglobin," Journal of Chromatography, 1995, pp. 53-60, vol. 711.

Murphy, S.J. et al., "An Evaluation of Cell Separation Techniques in a Model Mixed Cell Population," Journal of Cell Science, 1992, pp. 789-798, vol. 102.

Olofsson, B. "Rho Guanine Dissociation Inhibitors: Pivotal Molecules in Cellular Signalling," Cell Signal, 1999, pp. 545-554, vol. 11, No. 8.

Olsvik, R. et al., "Magnetic Separation Techniques in Diagnostic Microbiology," Clinical Microbiology Reviews, Jan. 1994, pp. 43-54, vol. 7, No. 1.

Phillips, T.M et al., "High-Performance Affinity Chromatography: a Rapid Technique for the Isolation and Quantitation of IgG from Cerebral Spinal Fluid," Journal of Chromatography, 1984, pp. 173-179, vol. 317.

Pilz, R.B. et al., "Isolation and Characterization of HL-60 Cells Resistant to Nitroprusside-induced Differentiation," The Journal of Biological Chemistry, Dec. 23, 1994, pp. 32155-32161, vol. 269, No. 51.

Pilz, R.B. et al., "Chemically-Induced Murine Erythroleukemia Cell Differentiation is Severely Impaired When cAMP-Dependent Protein Kinase Activity is Repressed by Transfected Genes," The Journal of Biological Chemistry, Aug. 15, 1992, pp. 16161-16167, vol. 267, No. 23.

Prigent, S.A. et al. "Enhanced Tumorigenic Behavior of Glioblastoma Cells Expressing a Truncated Epidermal Growth Factor Receptor is Mediated Through the Ras-Shc-Grb2 Ppathway," The Journal of Biological Chemistry, Oct. 11, 1996, pp. 25639-25645, vol. 271, No. 41.

Prince, H.E. et al., "Preparation of $CD8^{bright}$ and $CD8^{dim}$ Lymphocyte Populations Using Two Positive Selection Methods in Tandem," Journal of Immunological Methods, 1993, pp. 139-148, vol. 165.

Satoh, T. et al., "Function of Ras as a Molecular Switch in Signal Transduction," The Journal of Biological Chemistry, Dec. 5, 1992, pp. 24149-24152, vol. 267, No. 34.

Schönthal, A. et al., "Requirement for fos Gene Expression in the Transcriptional Activation of Collagenase by other Oncogenes and Phorbol Esters," Cell, Jul. 29, 1988, pp. 325-334, vol. 54.

Sharma, P.M. et al., "Inhibition of Phosphatidylinositol 3-Kinase Activity by Adenovirus-Mediated Gene Transfer and Its Effect on Insulin Action," The Journal of Biological Chemistry, Jul. 17, 1998, pp. 18528-18537, vol. 273, No. 29.

Suhasini, M. et al., "Cyclic-GMP-Dependent Protein Kinase Inhibits the Ras/Mitogen-Activated Protein Kinase Pathway," Molecular and Cellular Biology, Dec. 1998, pp. 6983-6994, vol. 18, No. 12.

Von Lintig, F.C. et al., "Ras Activation in Human Breast Cancer," 2000, pp. 51-62, vol. 62.

Zohn, I.M. et al., "Rho Family Proteins and Ras Transformation: the RHOad Less Traveled Gets Congested," Oncogene, 1998, pp. 1415-1438, vol. 17.

* cited by examiner

SOLID PHASE ISOLATION OF PROTEINS, NUCLEIC ACIDS AND OTHER MACROMOLECULES

CROSS REFERENCE TO RELATED APPLICATIONS

This application claims the benefit of priority of U.S. provisional application Ser. No. 60/443,231 filed Jan. 28, 2003 which is incorporated herein by reference in its entirety.

GOVERNMENT INTEREST

This invention was made with government support under CA76968 awarded by the National Institutes of Health. The government has certain rights in the invention.

BACKGROUND OF THE INVENTION

Solid-phase capture and affinity purification have a wide variety of applications in research, clinical, and pharmaceutical laboratories. For the batch analysis of multiple samples, a capture reagent (e.g., an antibody) can be immobilized on the bottom of microtiter plate wells to bind a molecule of interest (e.g., the corresponding antigen). This system provides a relatively small surface area for capture and a small working volume during binding and washing of the target molecule. Such assays allow for the determination of the presence of a molecule in a sample, but do not typically allow for the isolation of a sufficient quantity of a molecule to perform further tests. Moreover, it is difficult to remove the molecule of interest from microtiter plates. Microtiter plates are typically made of clear, polystyrene plastic to allow for colormetric assays to be performed. Polystyrene is not stable in the presence of a variety of organic compounds frequently used for elution. Additionally, the plates cannot be heated to elute the samples into loading buffer for analysis of the samples by SDS-polyacrylamide gel electrophoresis (PAGE).

A higher surface area for solid phase capture can be obtained by the use of microbeads coated with the capture reagent. Microbeads made of any of a number of materials for attachment of a variety of capture reagents have been reported. One of the most commonly used polymer microbeads are agarose microbeads. Frequently, either protein A or protein G is attached to the beads through a linking reagent such as cyanogen bromide for capture of antibodies on the beads. The antibodies captured on the protein A or protein G coated beads can subsequently be used as capture reagents for capture of the antigen corresponding to the antibody.

A number of other microbeads have been reported in the literature including magnetic beads (i.e. polystyrene-coated paramagnetic iron beads, M-450 Dynabeads) for the capture of monoclonal antibodies (Quitadamo and Schelling, *Hybridoma*, 17:199-207. 1998; incorporated herein by reference); particulate nitrocellulose for the capture of a variety of proteins (Hammerl et al., *J. Immunol. Meth.*, 165:59-66. 1993, incorporated herein by reference); protein A Superose (crosslinked agarose) beads (Leibl and Erber, *J. Chromatogr.*, 639:51-56.1993, incorporated herein by reference), protein A polyhydroxyethylmethacrylate beads (Denizli et al., *J. Chromoatogr. B*, 668:13-19.1995, incorporated herein by reference), and alginate-chitosan beads (Albarghouthi et al., *Int. J. Pharm.*, 206:23-34. 2000, incorporated herein by reference) for the capture of immunoglobulins; and glass beads for the capture of antibodies (Phillips, *J. Biochem. Biophys. Methods*, 49:253-262. 2001, incorporated herein by reference) and single stranded DNA (Walsh et al., *J. Biochem. Biophys. Methods*, 47:221-231, incorporated herein by reference). A number of additional beads and linking reagents are shown in Table 1 and Table 2 from Nisnevitch and Firer (*J. Biochem. Biophys. Methods.* 49:467-480. 2001, incorporated herein by reference). The higher surface area of the beads as compared to the microtiter plate allows for the capture of a substantially larger quantity of the molecule of interest. Such affinity purification methods are powerful techniques and can be used for a number of purposes including determining the presence and quantity of a macromolecule in a sample, determining the rate of a macromolecule's synthesis and degradation, identifying complexes of macromolecules and purifying small amounts of macromolecules.

The use of these techniques is limited both by the cost of the reagents required (e.g. protein A- or protein G-agarose) and the amount of effort required to perform the assays. As opposed to microtiter plates that can be filled with wash buffer using a multichannel pipettor and the buffer removed by inversion of the plate, samples purified on beads must be handled individually and with care. Each individual tube must be filled with buffer, mixed to resuspend the beads, centrifuged briefly to collect the beads at the bottom of the tube and the buffer aspirated carefully so as not to aspirate the beads. This limits the number of samples that can be processed by an individual at one time and makes automation of the process difficult. Due to the number of washes required, it is not practical to process more samples than can be placed in a single microfuge rotor, typically 18. Moreover, many macromolecules and macromolecular complexes are labile. To increase the stability of the molecules and complexes, immunoprecipitation assays are often performed in a cold room (4° C.), which is both uncomfortable and impractical.

Solid phase capture assays using beads may also be performed by column chromatography. The macromolecule of interest is captured on beads coated with the capture reagent by batch binding or by passing a mixture containing the molecule of interest over a column. Although such methods are somewhat more amenable to automation, elution of the molecule of interest from the column requires a relatively large amount of buffer, frequently resulting in a solution of the molecule of interest that must be concentrated before further analysis. This is time consuming and can result in deterioration of the sample.

SUMMARY OF THE INVENTION

The invention is a method for isolating macromolecules comprising coating the inner walls of a test tube with beads to a predetermined level; coating the beads with a capture reagent of the macromolecule of interest; incubating the coated beads with a solution containing the macromolecule under conditions to allow binding of the macromolecule to the capture reagent; washing the coated beads with the bound macromolecule with a wash buffer to remove unbound material while maintaining binding of the macromolecule to the binding partner; and eluting the macromolecule from the binding partner. This method allows for affinity purification of macromolecules in a substantially more rapid fashion than more typical immunoprecipitation methods, column chromatography or other methods in which a capture reagent attached to beads for isolation of a macromolecule of interest wherein the beads are not attached to a solid support.

The invention is the tubes for use in the instant invention. The tubes are plastic tubes, preferably 1.5 ml polypropylene, screwcap microcentrifuge tubes, coated with a monolayer of beads on the bottom portion of the inner surface of the tube.

The beads may be any of a number of materials including, but not limited to glass or polymer.

The invention is the method of preparation of the tubes for use in the instant invention. The tubes for use in the invention are typically polypropylene microfuge tubes; however, any tube with appropriate melting characteristics and of a scale appropriate for the isolation of the macromolecule of interest can be used. The tubes may be coated with glass beads or polymer microbeads such as agarose beads. In the case of glass beads, the beads are heated to a temperature such that they melt a superficial layer of the tube allowing the beads to attach to the sides of the tube. The unattached beads are removed by inverting the tube. In the case of the polymer microbeads, the tubes are heated in a predetermined region, typically to a predetermined height around the circumference of the tube, to melt the superficial layer of the inside wall of the tube before the dry beads are introduced into the tube. The tube is filled with beads that adhere only to the melted portion of the surface of the tube. Unbound beads are removed, typically by inverting the tube.

The invention is an apparatus for making the glass bead coated tubes. An apparatus for preparation of glass bead coated tubes comprises a container with a top opening for heating glass beads; a heating element in functional contact with the container; a first conduit with a first and second end, wherein the first end of the conduit is functionally connected to the top opening of the container and the second end of the conduit is shaped to fit snugly inside a tube to be coated with beads; and a pivotable rod functionally attached to the container to allow the container to be rotated vertically through at least about 180 degrees.

The invention is a method isolating guanine nucleotide-binding proteins for determination of guanine nucleotide ratios comprising, coating an interior surface of a test tube with a defined quantity of glass beads wherein the beads have a surface; reacting the beads with an agent to modify the surface of the beads to provide a plurality of free amino groups; reacting the free amino groups on the beads with a bifunctional amine cross-linker to provide a plurality of sites for binding a guanine nucleotide-binding protein binding partner (e.g. an antibody); incubating the coated beads with a solution containing the guanine nucleotide-binding protein under conditions to allow binding of the guanine nucleotide-binding protein to the binding partner while inhibiting nucleotide hydrolysis or release; washing the coated beads with the bound guanine nucleotide-binding protein with a wash buffer to remove unbound material while maintaining binding of the guanine-nucleotide binding protein to the binding partner and inhibiting nucleotide hydrolysis and release; releasing the bound nucleotide from the guanine-nucleotide binding protein; and determining the ratio of guanine nucleotides released from the guanine nucleotide-binding proteins.

TABLE 1 lists characteristics of the more common antibody immobilization procedures for use in affinity chromatography;

TABLE 2 lists reagents used for covalent, non-oriented immobilization of antibodies;

TABLE 3 are the data from the nucleotide ratio experiments in Example 6.

The present invention will be better understood from the following detailed description of an exemplary embodiment of the invention, taken in conjunction with the accompanying drawings in which like reference numerals refer to like parts and in which:

DETAILED DESCRIPTION OF THE DRAWINGS AND PREFERRED EMBODIMENTS

Definitions

A capture reagent is a molecule that has a sufficiently high specificity and affinity for a molecule of interest or domain of a molecule of interest to bind the molecule of interest with at least about 10-fold preference over other components of a mixture. Examples of pairs of capture reagent-molecule of interest include, but are not limited to antibody-antigen; strepavidin-biotin; hexahistadine domain-nickel; and glutathione-glutathione-S-transferase. Affinities ($K_a$) of antibodies for their antigens are in the range of about $10^5$ to $10^{12}$ per mole.

Conditions to allow for binding are well known to those skilled in the art for various capture reagents and their binding partners. To a large extent, the best conditions for binding must be determined empirically; however, binding of biological molecules to each other typically occurs under physiological conditions, i.e. pH of about 7.4 and salts of about 150 mM. Variations in pH, ionic strength and the presence of detergents, chaotropic ions and organic molecules can alter binding between capture reagents and their binding partners. Methods and considerations for optimizing binding between partners is taught in any of a number of references including *Using Antibodies: A Laboratory Manual* by Ed Harlow and David Lane (Cold Spring Harbor Laboratory Press, copyright 1999). Such methods are well known to those skilled in the art.

A cross-linking reagent is a chemical, typically commercially available (e.g. Pierce Biotechnology), that can be used to link molecules through specific chemical groups. Most cross-linking reagents have two reactive groups connected by a flexible spacer arm. The reagents differ in their spacer arm length, cleavablitiy and reactive groups. Cross-linkers may have the same (homo-bifunctional) or different (heterobi-functional) functional groups at opposite ends of the linker arm. Some cross-linking reagents contain a third functional group to allow for a detectable label to be added or to allow the formation of trimeric complexes. Functional groups include, but are not limited to, primary amine reactive, sulfhydryl, sulfhydryl addition or disulfide reduction, carbohydrate reactive, carboxyl reactive and photoreactive (non-selective).

A linker molecule is a molecule that is used to attach the capture reagent either directly or indirectly to the beads. Frequently a series of linker molecules are used to attach the capture reagent to the beads. In the case of glass beads, 3-aminopropyltriethoxysilane is used to treat the beads to generate reactive amines on the surface of the beads for reaction with the cross-linking reagent which is then attached to the capture reagent. The cross-linking reagent can also be considered a linker molecule as it attaches the capture reagent to the beads. In the case of agarose beads, cyanogen bromide (CNBr) is used to treat the beads to allow for attachment of protein molecules, frequently protein A or protein G. Similarly, the protein attached to the CNBr can also act as a linker molecule, attaching a second protein, such as an antibody, to the beads.

A macromolecule is any protein, peptide, oligonucleotide, carbohydrate, polymer or other organic molecule that can be specifically recognized by a capture reagent.

The melting point of the surface of the tube is the temperature at which the surface of the tube is sufficiently melted to allow polymer beads to stick without being hot enough for the tube to become misshapen or to cause the beads to melt. Typically about 150° C. is the melting point of the surface for standard, 1.5 ml polypropylene, screwcap microcentrifuge tubes that are preferred for use with the instant invention. However, due to variation in tubes both within and between manufacturers, the melting point of the tubes must be tested for each batch of tubes. Additionally, the parameters for application of heat vary on the amount of area to be heated, with higher temperatures and shorter heating times used for heating small portions of the tube, and lower temperatures for longer times to heat larger portions of the tube. Such considerations are well known to those skilled in the art. The melting point of the tubes and the conditions used to melt the tubes are not limitations of the instant invention.

Determination of the melting point is most commonly performed by heating the surface of tube retained in a support to about an average melting temperature (e.g. about 150° C.) for a predetermined amount of time (e.g. 2-10 seconds), removing the tube from the support, and touching the inner surface of the tube with a rigid object (e.g. metal or glass rod) and applying gentle pressure to determine if the tube is sufficiently sticky to allow the polymer beads to stick without being deformed. Such testing is routine and well within the ability of those skilled in the art.

Polymer microbeads are any of a number of microbeads with diameters of about 100-600 microns in diameter that are commercially available from a number sources (e.g. Pharmacia, Sigma Chemical Company, Calbiochem and ICN) for use as supports for solid phase capture. Alternatively, the beads may be made by the end user (see, for example Albarghouthi et al., 2000) Examples of such beads include, but are not limited to agarose, alginate, cellulose, nitrocellulose, polyhydroxyethylmethylacrylate, dextran, acrylic and nylon. Beads can also be purchase already coated with linking agents (e.g., CNBr agarose). Dry beads are preferred for use with the method of the invention.

Detailed Description

The invention is a method to perform solid phase capture in tubes, preferably 1.5 ml screwcap microcentrifuge tubes, by immobilizing the capture reagent on beads bonded to the inner surface of the wall of the tube. The beads provide a relatively large surface area as compared to the tube alone, and because the tubes are preferably made of polypropylene, they can be heated to high temperatures (e.g. boiling). The capture reagent is covalently bonded to the beads by at least one linker molecule, thereby providing a highly stable covalent linkage. This method allows for rapid and efficient washing of the beads binding the captured molecule of interest and lends itself to full automation.

The tubes of the invention are prepared by different methods depending on the type of bead used. Preparation of glass bead coated tubes can be performed in a number of ways, from a fully manual to an fully automated system. Regardless of the exact method or apparatus used to make the tubes, the concept is the same. A plurality of beads in excess of the number required to coat the tube are heated. The hot beads are then transferred into the tube through a hollow conduit (e.g., a funnel) wherein one end of the conduit is shaped to facilitate pouring in the beads and the other end is sized to fit snugly into the tube to be coated with beads. This allows for all of the tubes to be filled to the same height resulting in approximately the same number of beads in each tube. Excess beads are poured out of the tube.

Figures 1, 2:
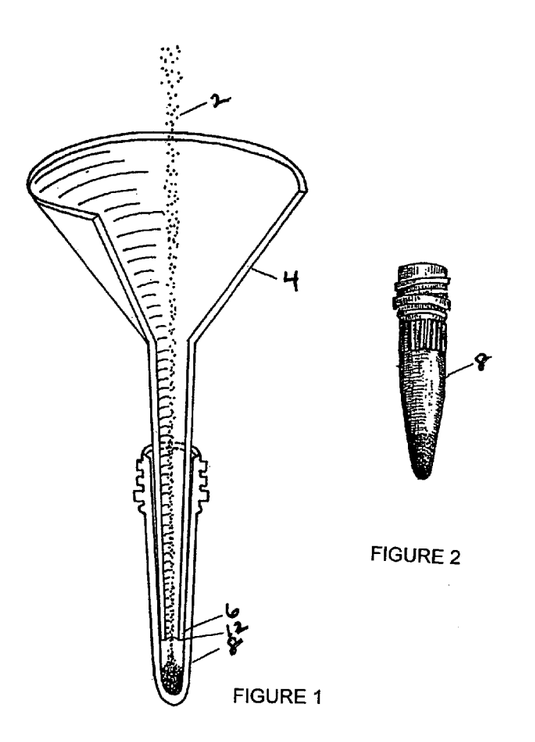
FIG. 1 illustrates a method for preparation of the glass bead coated tubes of the invention.
FIG. 2 is a glass bead coated tube of the instant invention.
Figure 3:
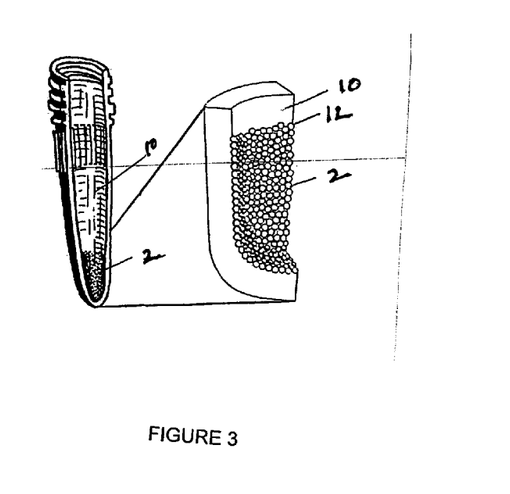
FIG. 3 is a cross section of a glass bead coated tube of the instant invention with an exploded portion of the interior surface of the tube.

The method in its most simple form is shown in FIG. 1. Heated glass beads 2 are poured through a funnel 4 with the end 6 shaped to fit snugly into the tube 8. Excess beads are poured out of the tube, preferably with the funnel still in place. The resulting tube is shown in FIG. 2. Cut-away and exploded versions of the tube are shown in FIG. 3. The inner surface of the tube 10 is evenly coated with a monolayer of beads 2 to a height 12 defined by the insertion of the funnel 4. The amount of beads in the tube can be readily altered by selecting a conduit to fit snugly into the tube at any defined height within the tube.

Figure 4:
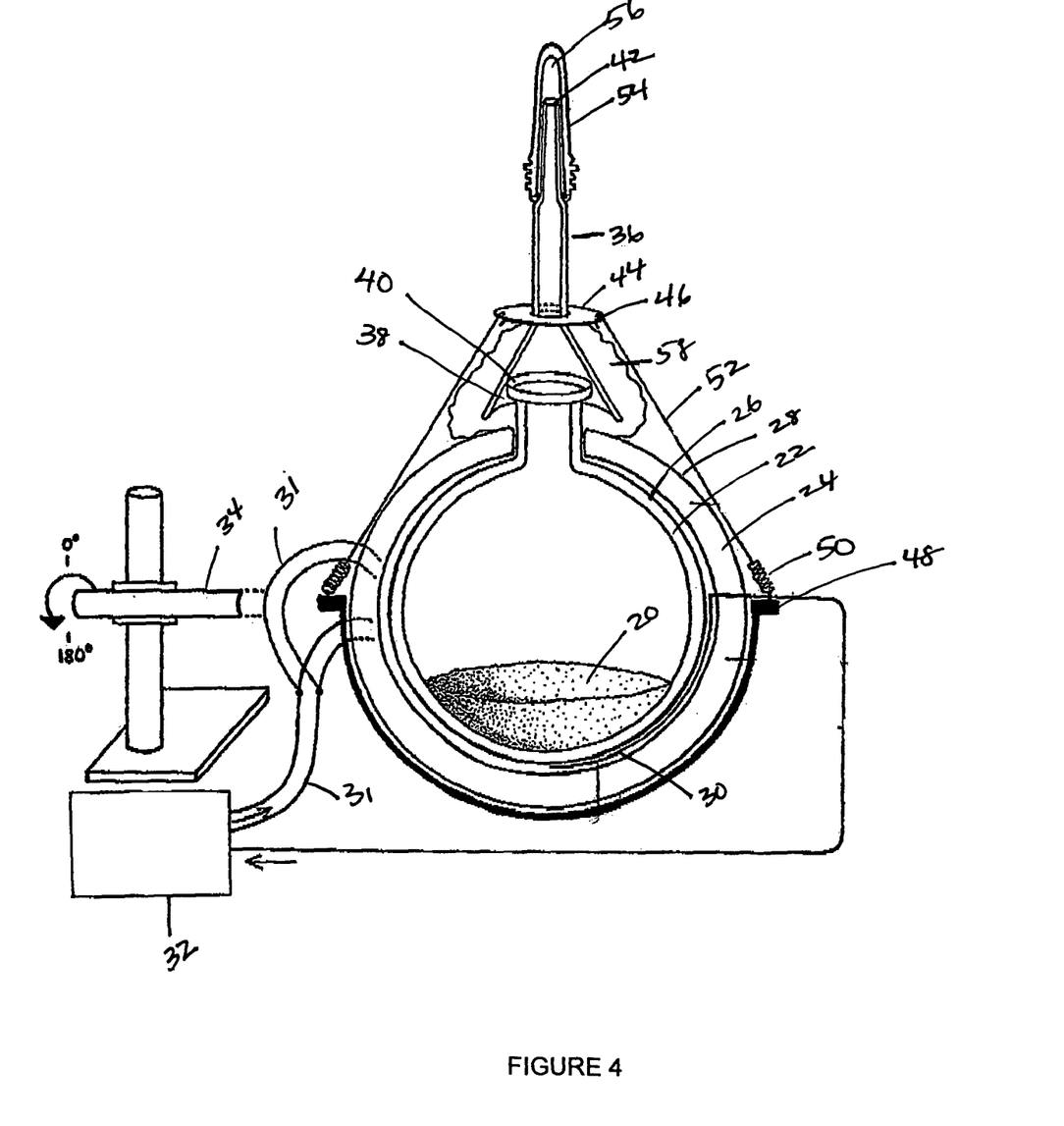
FIG. 4 is a cross section of an apparatus for the preparation of the glass bead coated tubes of the instant invention.

An apparatus for use in the preparation the glass bead coated tubes for the invention is shown in FIG. 4. The glass beads 20 are heated in a container 22 such as a round bottom flask which is inside a heating mantle 24 shaped to efficiently provide heat to the container. The upper portion of the container 26 is wrapped with a flexible mantle 28 to maintain the temperature of the beads throughout the tube preparation process. The flask is maintained at a temperature of about 450-460° C. by use of a heating element 30, preferably a K type thermocouple placed under the container 22 with the heating element connected to a power control 32 via an electrical connector 31 to regulate the voltage applied to the heating element. The container assembly is enclosed in an aluminum housing 48 that is mounted on a pivotable rod 34 so that the container can be rotated in a vertical plane through about at least 180 degrees to pour heated beads 20 out of the flask 22.

A first conduit 36, such as a glass funnel, is attached at a first end 38, to the opening of the flask 40 and fitted tightly to the flask opening. The second end of the conduit 42, points upwards, away from the flask 22. The conduit 36 is held tightly to the flask using a metal washer 44 which is slipped over the second end of the first conduit. The metal washer 44 has holes 46 drilled in it allowing it to be connected to the aluminum housing 48 that surrounds the heating mantle 24 via a spring loaded system comprised of springs 50 and wires or rods 52, preferably composed of stainless steel.

Glass beads 20 are introduced into the container 22 preferably via a second conduit (not shown) which has a first end that fits into the second end of the first conduit 42 and a flared second end to allow the beads to be easily poured into the conduit. Once the beads are heated, a tube 54, preferably a 1.5 ml screwcap microcentrifuge tube, is fitted snugly on the second end of the first conduit 42 and the container is turned about 180° around a horizontal axis to invert it, allowing the beads to pass through the first conduit 36 and into the tube 42 to coat the inner walls at the bottom of the tube 56. The container is then returned to the original orientation, and the beads that have not stuck to the walls of the tube are returned to the container. The tube is removed and a new tube is placed on the second end of the first conduit and the process is repeated indefinitely until a sufficient number of tubes for the desired application have been prepared.

In a preferred embodiment, a large reservoir of heated glass beads are retained in the container 22. Therefore, the small number of beads that return to the flask after each cycle have little, if any, effect on the temperature of the beads in the flask. Moreover, the first conduit is wrapped in glass wool 58 as an insulator so that the loss of heat by the glass beads during each cycle is minimal. Using the apparatus described above, a finished tube with immobilized beads can be produced about every 10 seconds. Such an apparatus can be well adapted to full automation for production of bead-lined tubes.

Preparation of polymer coated beads can be performed in a number of ways depending on the equipment available. The method has essentially two steps, melting a defined portion of the tube, typically the inner surface near the bottom of the tube, and transferring the beads into the tube. Any of the heating steps can be combined with any of the bead transfer steps. The exact method of the preparation of the tubes is not a limitation of the tubes prepared for use in the invention or the purification methods of the invention.

The melting point of the tube must be determined empirically for the tube to be used. The amount of heat required is dependent upon considerations including, but not limited to the material from which the tube is made (e.g. polypropylene or polystyrene), the thickness of the wall of the tube. In all methods, a defined quantity of heat is applied for a defined period of time to a portion of a tube in a holder that may or may not be designed for cooling the outer surface of the tube. Immediately after heating, the tube is removed from the holder and tested by applying gentle pressure to the inner surface of the tube using a rigid implement, such as a glass or metal rod, to determine if the surface of the tube is sufficiently melted for attachment of the polymer microbeads. Under light pressure, the tube should be sticky, but there should be no deformation of the overall shape of the tube. Determination of the amount of heat and time required to melt the surface of the tube is routine experimentation and well within the ability of those skilled in the art.

The interior surface of the tube can be heated using a heat gun comprised of a heat resistant, hollow tube (e.g. copper) attached to a source of hot air. Preferably, the tube is placed in a cooling block or holder to prevent the outer surface of the tube from deforming.

The interior surface of the tube can be heated by placement of an insulated heating filament attached to a power source inside the tube. Preferably, the filament is passed through a solid, insulated rod (e.g. ceramic) with two holes of sufficient diameter to allow the filament to be passed through the first hole through a first bottom opening and then bent to be passed through the second bottom opening and up through the second top opening, leaving a loop extending beyond the bottom of the rod and providing sufficiently long ends on the top of the rod for attachment to a power supply. Alternatively, a loop of filament can be passed through a hollow rod that is packed with insulation to separate the strands of filament. Preferably, the loop of filament extending beyond the bottom of the rod is shaped to mimic the shape of the interior surface of the bottom of the tube to provide even heating of the surface.

Figure 5:
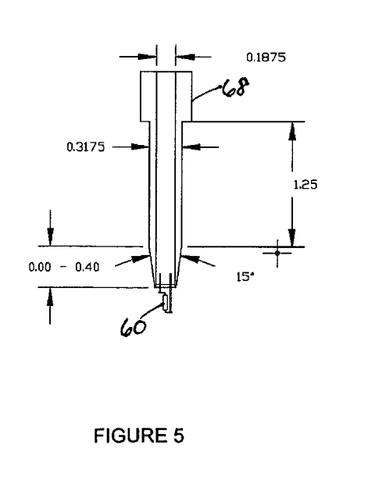
FIG. 5 is a schematic of the infrared filament for placement inside the tube.
Figure 6:
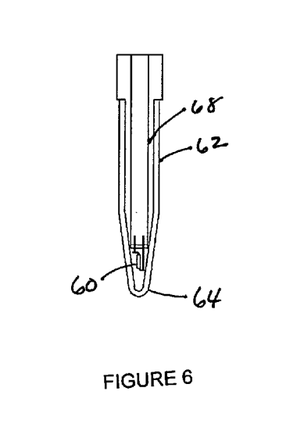
FIG. 6 is a schematic of the infrared filament inside the tube.

In a preferred embodiment, a small infrared light (IR, wavelength 0.5-50 microns) source 60 is placed inside the tube 62 near the bottom of the tube 64 to melt the surface 66. Preferably the IR emitter 60 is mounted upon an insertion guide 68 designed to direct the filament into the tube and hold it at a constant distance from the bottom of the tube. Metals, ceramics, high temperature resistant polymers are suitable for this application. The insertion guide is machined to match the size and shape of the inner surface of the tube, in a manner similar to the funnel for delivery of glass beads, so that the placement of the filament is at the desired height within the tube, typically 0.5 to 5 mm from the bottom of the tube. The overall length value of the guide is easily adjusted for placement of the beads within any region of the tube. The amount of surface that can be covered with beads is dependent on the size and intensity of the IR light source.

Figure 7:
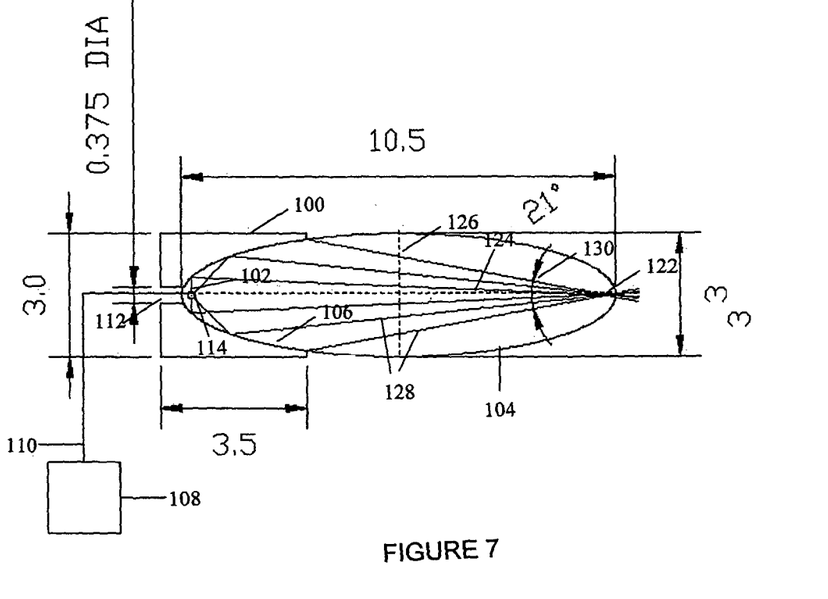
FIG. 7 is a schematic diagram of a cross sectional view of an infrared light and an elliptical reflector for heating the interior walls of tubes.
Figure 8:
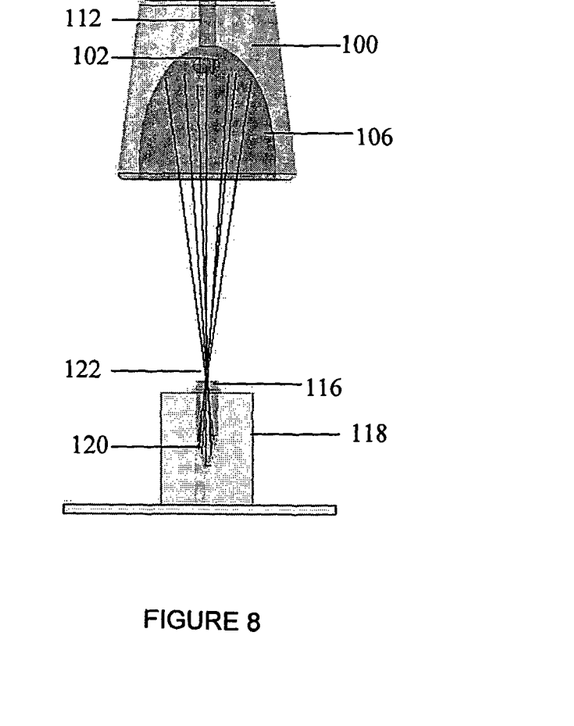
FIG. 8 is a perspective view of an infrared light and elliptical reflector apparatus for heating the interior walls of tubes.

Alternatively, IR light or laser can be used to heat the inner surface of the tube. The text and drawings refer to an IR light source, but a similar configuration can be used with a laser. An apparatus for heating the tube surface using an elliptical reflector 100 and an IR source 102 is shown in FIGS. 7 and 8. An ellipse 104 is defined by the inner curve 106 of the reflector. All ellipses have two foci. The IR light source 102 attached to a power supply 108 by an appropriate connector 110 is inserted through an opening 112 in the reflector, co-linear with the major axis 124 of the ellipse, and placed at the first focus 114 of the ellipse, closer to the reflector. A tube 116 is placed in a holder 118 in a path co-linear with the major axis of the ellipse. The portion of the tube to be melted 120 is placed just beyond the second focus 122, further away from the reflector, at a distance to allow heating of the desired portion of the tube. The portion of the tube being heated by the IR light can be easily determined as many IR emitters also emit visible light. Alternatively, an IR detector can be used. Such apparatuses for focusing light and IR detection are well known to those skilled in the art.

Elliptical reflectors are commercially available or can be readily made using any of a number of methods, preferably using computer aided design and a numerical controlled lathe. The surface of the reflector is polished to a mirror finish to result in maximal reflection of IR light. In the experiments presented herein, the reflector was made of aluminum which was selected for its high reflectivity of infrared light, workability and relatively low cost. Other reflective materials and coatings that can be used in the context of the invention are well known to those skilled in the art.

The ratio of the lengths of the major 124 to minor 126 axes are dependent upon the size of the tubes to be used and the angle of the walls to each other in the conical portion of the tube. In the preferred embodiment, the ellipse must be relatively narrow, resulting in an f-ratio (focal length to aperture) of about 2.5 to 5 to produce infrared light in a beam 128 through an angle 130 that is sufficiently narrow to reach the bottom of the preferred microcentrifuge tubes of the invention (about 21°). The beam may also be narrowed by use of an aperture (not shown) in the light path to decrease the angle of the reflected light and reduce scatter. The use of an aperture can be beneficial as the IR source is an elongated source rather than a point source, resulting in unavoidable scatter. Methods of modification of elliptical reflectors to direct light to various surfaces is well known to those skilled in the art.

The overall size of the ellipse is determined predominantly by convenience considerations and the strength of the IR source. The ellipse should be sufficiently large to allow for ease in insertion and removal of tubes in the path of the beam. However, it should also be small enough to allow for easy fabrication of the reflector and for bench top use.

The reflector used for the preparation of polymer bead-lined tubes herein defined an ellipse with a major axis of 10.5 inches and a minor axis of 3.5 inches. The three-dimensional ellipse was formed by rotation around the major axis (FIG. 7). The length of the reflector was 3.5 inches with the opening at the end of the major axis being a circle with a diameter of 0.375 inches for insertion of the IR light source. Methods for determining the size of the ellipse based on the desired distance between the foci and the angle of light to be reflected are well known to those skilled in the art.

Once the tubes are heated, the beads must be promptly transferred into the tube. Beads can be transferred into the tube using a solid rod slightly narrower than the inner diameter of the tube with the end of the rod shaped to fit snugly into the portion of the tube to be coated with the polymer beads. The shaped rod is coated homogeneously in beads using one of a number of different strategies and then pressed gently into the portion of the tube to be coated. The rod is removed and any unattached beads are removed. This is typically done by inverting the tube and tapping it on a solid surface.

The shaped rod can be coated with beads using any of a number of methods. The rod can be moistened with water or other appropriate buffer before dipping it in the polymer beads to cause the beads to adhere. This method is not preferred as the beads become wet and clump, making it difficult to form continuous, homogeneous layers of beads.

As the beads are light, they can be adhered to the shaped rod using electrostatic energy. This can be accomplished by use of a high voltage multiplier circuit (e.g. a Cockroft-Walton voltage multiplier) or a Vandegraaff generator to charge the rod. Preferably the rod is composed of two different materials with the tip to be coated being made of a material that can easily be charged and the end to be held made of a material that is not easily charged or that is insulated with rubber or other material to prevent transfer of energy. The shaped end of the rod is charged by contacting the circuit, dipped in beads and inserted into the heated tube and pressed to adhere the beads.

The shaped portion of rod can be formed of a porous material wherein the pores are smaller than the polymer beads (e.g. aluminum oxide, ceramic). The shaped portion of the rod is attached to a non-porous rod with an opening extending from the interface with the porous shaped portion to a connector for a vacuum line. Alternatively, the rod may be formed completely of porous material with the non-shaped portion being coated to block the pores on the sides, but not at the end of the rod where it can be attached to a vacuum line. A vacuum is applied to the rod that is dipped into the polymer beads. The rod is then inserted into the tube and pressed to adhere the beads while simultaneously while simultaneously turning off the vacuum.

In a preferred embodiment, beads are poured into the tube and allowed to adhere for 5-10 seconds before the excess beads are removed. The beads adhere only to the portion of the tube that has been heated.

Once the polymer bead coated tubes are prepared, the beads are treated essentially in the same manner as they would be treated if they were free-floating in the tube. Tubes with adhered dried beads can be stored under conditions that would be used for the storage of free beads (e.g. room temperature of agarose, 4° C. for CNBr agarose). Linking agents, cross-linking agents and capture reagents are attached to the beads using the same reagents that would be used if the beads were not attached to the tubes. Such methods are well known to those skilled in the art.

The method for attaching the capture reagent to the beads depends on the type of beads used. Tables 1 and 2 include a number of the common antibody immobilization procedures for use in affinity chromatography from a review by Nisnevitch and Firer (2001). Table 1 includes methods that are more specifically applicable to attachments of antibodies to solid supports; however, methods of attachment of the antibodies through their carbohydrate moieties can be used for any of a number of carbohydrate modified proteins or for carbohydrates themselves. Table 2 includes a series of solid phases, that can be modified using linker molecules (as described in the solid phase column) to generate reactive groups to couple the antibodies to be coupled using the agents listed to the functional groups on the antibodies. Amine groups and carboxylic groups are available on essentially all proteins. Using heterobifunctional cross-linking agents with the solid phase supports listed in Table 2, essentially any capture reagent could be attached to at least one solid support.

Selection of a cross-linking reagent is a matter of choice. Selection guides such as *Double-Agents™ Cross-Linking Reagents Selection Guide*, published by Pierce Biotechnology, Inc. (incorporated herein by reference) teaches a large number of commercially available agents and relevant issues to consider in selection of a cross-linking reagent such as selectivity of the reactive group, spacer arm length, solubility, membrane permeability and cleavability. The instant invention is not limited by the selection of a linker molecule or cross-linking reagent. The selection of a solid support, linker molecule and cross-linking reagent are dependent on the capture reagent and the molecule of interest to be captured. Selection of the solid support, linker molecule and cross-linking reagent is a matter of choice and well within the ability of those skilled in the art.

A series of experiments were performed to demonstrate that the bead coated tubes of the instant invention function similarly to more commonly used reagents such as protein A- and protein G-agarose beads for immunoprecipitation, and as a proof of principle for the methods of the invention. Two different proteins were immunoprecipitated from cultured cells, Ras and the guanine dissociation inhibitor of Rho (Rho-GDI). Ras is a guanine nucleotide binding protein that alternates between the active GTP-bound state and the inactive GDP-bound state. It is genetically activated in about 30% of human cancers and an activated Ras can induce cell transformation in a model cell system. Rho is also a guanine nucleotide binding protein that is involved in cell morphology and motility. The glass-bead coated tubes of the instant invention were also used in an assay to determine the activation state of Ras in a number of cultured cell lines. Both the immunoprecipitation and determination of Ras GTP-GDP ratio experiments demonstrated that the immobilized glass beads are equivalent or superior to standard techniques using agarose beads for immunoprecipitation, and that the glass beads provide more rapid processing of samples. The method of the invention has wide applicability for the isolation of macromolecules from cell and tissue extracts and other solutions.

Example 1

Bonding of glass beads to the inner walls of microcentrifuge tubes. Acid-washed glass microbeads, 425-600 μm diameter, were obtained from Sigma-Aldrich Co.; 3-aminopropyltriethoxysilane and dimethyl suberimidate were from Pierce Chemical Co.; and conical polypropylene microcentrifuge tubes [12.6 mm (O.D.)×47.6 mm (L), 1.5 ml volume, screw-cap with O-ring] were from Fisher Scientific.

Glass microbeads were heated to 455° C. in a round bottom flask by upper and lower heating mantles under control of a microprocessor-controlled temperature regulator. The heated beads were added to microcentrifuge tubes by pouring through a glass funnel inserted into the tubes (see FIG. 1). The high temperature of the beads melted the superficial layer of the inner wall of the tubes, and the beads became bonded to the tube wall; excess beads which did not bond to the tubes were returned to the round bottom flask. Within the tapered portion of the microcentrifuge tubes, the height of the beads could be precisely regulated by grinding the stem of the funnel to fit snugly within the tube. The bead height was approximately 0.7 cm above the bottom of the tube for the experiments presented herein except where indicated. Thus, approximately one-fifth of the tube length was lined with beads, and at this height, there were approximately 1000 glass beads bonded to the walls of each tube. The entire inner wall of the tubes could be lined by beads by placing the funnel just inside the tube opening.

The glass beads formed a dense monolayer of beads bonded to the inner wall of the tubes. At the working temperature, the glass beads were sufficiently hot to melt the superficial layer of the tube wall, but the beads themselves did not melt. Thus, the beads remained spherical and did not adhere to each other. This allowed for uniform spacing of the beads and maximized the surface area of the beads that was available for subsequent reaction with a silane compound. In addition, as can be noted in FIG. 3, the beads were bonded circumferentially to the wall of the tube, leaving the lumen of the tube empty which provided for efficient washing of the beads.

The beads were demonstrated to be tightly bonded to the tube wall by three criteria: first, <0.1% of the beads were released from about 100 tubes turned upside down and tapped hard on the outside wall with a metal spatula; second, inserting a metal rod into 20 tubes and vigorously scraping the inside walls released <1% of the beads; and third, heating tubes to 100° C. for 5 min (as described below) did not release any beads from the tubes.

Example 2

Immobilization of protein A or protein G on glass Microbeads. After bonding the glass microbeads to the wall of the centrifuge tubes, protein A or G was immobilized on the glass beads. To accomplish this, free Si groups on the bead surface were first reacted with aminopropyltriethoxysilane to yield free amino groups; aminopropyltriethoxysilane diluted 1:5 in acetone was incubated at room temperature for 5 min with the bonded beads, and the beads were washed three times with acetone and three times with 100 mM Hepes, pH 7.4. The homobifunctional imidoester dimethyl suberimidate was then used to cross-link the free amino groups on the surface of the glass beads to amino groups of protein A or G. This reaction proceeded for 1 h at 4° C. using 1 mM dimethyl suberimidate and 1 mg/ml of protein A or G in 100 mM Hepes, pH 8.5. Under these conditions, the preferred reaction is with the α-amines of the proteins rather than with epsilon amines of glutamine and asparagine. The reaction was stopped by adding Tris-HCl, pH 7.4, to a final concentration of 100 mM (Tris buffer); the protein A-coated beads were washed three times with Tris buffer and then phosphate-buffered saline containing 0.01% sodium azide was added to the tubes for storage.

Example 3

Quantitation of protein A binding sites on glass microbeads. The number of protein A binding sites on the glass beads bonded to the wall of microcentrifuge tubes was determined by two different methods. In the first method, 50 µg of rabbit IgG in HNMN buffer (50 mM Hepes, pH 7.5, 150 mM NaCl, 5 mM $MgCl_2$, 1% Nonidet P-40) was added to the tubes, and the tubes were shaken gently for 2 h at 4° C. to allow for binding of the rabbit IgG to the immobilized protein A. The beads were washed three times with Tris buffer and IgG bound to the beads was measured by the Bradford method using bovine serum albumin as a standard.

In the second method, 2-10 µg of $^{125}$I-labeled rabbit anti-mouse IgG (specific activity 10 µCi/pg) was added to the tubes, and after a 1 hour incubation and six washes, the amount of immunoglobulin bound to the beads was determined by gamma counting and comparison to a standard curve.

Upon analysis of total protein bound to the glass beads, it was determined that 3.7±0.3 µg (mean±SD of six independent experiments) of rabbit IgG bound per tube. Because protein A is covalently linked to the glass beads, no protein was measured in tubes incubated with buffer alone. When the amount of protein A bound was measured by determining the amount or rabbit $^{125}$I-IgG bound to each tube, it was determined that approximately twofold more protein bound per tube, or 8.4±0.9 µg (mean±SD of three independent experiments) of IgG per tube. This twofold difference in IgG bound per tube is likely due to differences in methodology, since in one case protein was measured by the Bradford method using bovine serum albumin as a standard, and in the other case, radioactivity was measured in a gamma counter. Based on the above measurements, we calculate that approximately 25-60 pmol (or $1.4-4.1\times10^{13}$ molecules) of IgG were bound to the glass beads in each tube. This amount of IgG bound per tube was approximately one-half the amount of IgG that we found binds to 7.5 µl of commercial protein G-agarose beads, a volume of beads routinely used to immunoprecipitate Ras and other proteins.

Protein A and protein G bound to glass beads were found to be stable over time. When stored at 4° C., the protein A or G immobilized on the beads was stable for at least 6 weeks; although similar results were found with either protein A- or G-coated beads, results are reported with only protein A-coated beads because protein A is less expensive than protein G.

Example 4

Comparison of immunoprecipitation using glass and agarose beads. Glass beads bonded to the walls of microcentrifuge tubes and coated with protein A were prepared as described above and incubated for 2 h at 4° C. with either the rat monoclonal anti-Ras antibody Y13-259 or a rabbit polyclonal anti-RhoGDI antibody; prior to use, the beads with the bound anti-Ras antibody were washed twice with HNMN buffer, and the beads with the bound anti-RhoGDI antibody were washed twice with Tris buffer. Approximately $5\times10^6$ NIH 3T3 cells were extracted either in HNMN or Tris buffer containing 1 mM dithiothreitol, 2 mM EDTA, and protease inhibitors, and the extracts were centrifuged at 10,000 g for 2 min. The supernatants were added to the microcentrifuge tubes containing the antibody-coated glass beads, incubated for 1 h at 4° C., and washed four times with HNMN buffer containing 500 mM NaCl, 0.5% deoxycholate, and 0.05% SDS. During the washes, the tubes were placed in a soft foam rubber disk which held the tubes tightly; this allowed all tubes to be emptied simultaneously by turning the disk 180° C. and, when combined with a repipettor to add wash buffer, provided for washing up to 24 tubes in cycles of less than 30 s. The immunoprecipitates collected on the beads were heated to 100° C. in an electrophoresis buffer containing 1% sodium dodecyl sulfate, and the denatured proteins were separated by PAGE; western immunoblots were performed using methods well known to those skilled in the art using either a mouse monoclonal anti-H-Ras antibody or the rabbit polyclonal anti-RhoGDI antibody.

Immunoprecipitates were collected on protein A- or G-agarose beads in a similar fashion except washing of the beads was performed by the standard method of cycles of resuspension/centrifugation/aspiration.

For immunoprecipitation of RhoGDI, wild-type NIH 3T3 cells were used. For immunoprecipitation of Ras, NIH 3T3 cells stably transfected with a plasmid encoding activated Ras under control of a dexamethasone responsive promoter [NIH 3T3 LTR-cHa-ras(A) cells] were used. The amount of protein in the immunoprecipitates was determined by western immunoblotting.

It was found that the protein A-coated glass beads were at least as efficient as protein A- or G-agarose beads in immunoprecipitating both RhoGDI and Ras. Varying the amount of glass beads had no effect on the amount of protein immunoprecipitated or on the presence of contaminating proteins. Neither the polyclonal rabbit anti-RhoGDI antibody nor the mouse monoclonal anti-HRas antibody were specific for their respective proteins. The protein A-coated glass beads yielded fewer contaminating proteins than protein A-agarose beads.

Example 5

Immunoprecipitation of Ras from cell extracts. Cultured cells were harvested rapidly and lysed in HNMN buffer with a small aliquot of the cell lysate saved for measuring protein or DNA content as described below. Ras was immunoprecipitated from clarified lysates as described above using protein A-coated glass beads or protein G-agarose beads; although protein A- or G-coated glass beads yielded similar results, protein G-agarose beads yielded less background than protein A-agarose beads. Because the primary anti-Ras antibody Y13-259 is a rat monoclonal antibody, it does not bind well to either protein A or G, and thus, a secondary goat anti-rat IgG (Fc fragment specific) was included in all tubes. In addition to the experimental samples containing antibody Y13-259, blank samples containing rat IgG were included.

Example 6

Elution and measurement of GTP and GDP bound to Ras. The method for determining the activation of Ras used herein is well known (Boss, U.S. Pat. No. 5,741,636, incorporated herein by reference); therefore, it will only be described briefly. GTP and GDP bound to immunoprecipitated Ras were eluted by heating to 100° C. for 5 min in a TrisPO$_4$ buffer containing dithiothreitol and EDTA. It has been demonstrated by HPLC analysis that 5% of GTP or GDP are destroyed when heated at neutral pH. The tubes were cooled and centrifuged, and GTP was measured in the supernatants by converting it to ATP using ADP and the enzyme nucleoside diphosphate kinase (NDPK), with the generated ATP measured by the luciferase method. In replicate tubes the NDPK was omitted to check for ATP contamination. The reaction was started by adding the sample, and light emission was measured for 10 s using a photon counting luminometer. This method is exquisitely sensitive allowing as little as 1 fmol of GTP to be measured. The sum of GTP plus GDP was measured by converting GDP to GTP using phosphoenolpyruvate and pyruvate kinase; GTP is then measured as described and represents the sum of GTP plus GDP.

Ras activation was measured in three different cell types, HL-60 promyelocytic leukemic cells, MDA-MB-231 breast cancer cells, and wild-type NIH 3T3 cells, both using protein A-coated glass beads and by a standard technique using 7.5 µl of protein G-agarose beads. It has been shown previously that the method quantitatively measures the amount of GTP and GDP bound to Ras in immunoprecipitates, and since Ras exists intracellularly only in a nucleotide-bound state, the method provides a quantitative measure of the amount of immunoprecipitated Ras.

It was found that the protein A-coated glass beads consistently yielded higher amounts of Ras-bound GTP, and a higher sum of Ras-bound GTP+GDP, than the protein G-agarose beads even though the immunoglobulin binding capacity of the protein G-agarose beads was about twofold greater than for the protein A-coated glass beads (Table 3); the increase in guanine nucleotides recovered by the glass bead method was two- to fourfold higher than by protein G-agarose beads, depending on the cell type.

These data suggest that the total amount of nucleotide-bound Ras recovered from the glass beads was higher than that recovered from agarose beads; however, it was found that the two methods yielded similar amounts of Ras when assessed by Western blotting. In several experiments, Ras activation and the amount of Ras in the immunoprecipitates were measured by western blotting. Consistently, a several-fold increase in total guanine nucleotides bound to Ras was consistently found when measuring Ras activation using the glass beads compared to using protein G-agarose beads, yet the amount of Ras protein in the immunoprecipitates appeared to be similar on western blots. Again, 7.5 µl of protein G-agarose beads were used corresponding to twofold more immunoglobulin binding sites than on the protein A-coated glass beads. These results suggest that some of the Ras bound to the agarose beads is nucleotide free, possibly because of denaturation during isolation. Although more total guanine nucleotides bound to Ras were found using protein A-coated glass beads than protein G-agarose beads, the relative amounts of GTP and GDP found by both methods were approximately the same, yielding similar percentage activations (Table 3).

Example 7

Bonding of agarose beads to the inner walls of microcentrifuge tubes. An IR22V filament manufactured by Scitec (obtained from Hawkeye Technologies) was placed onto the end of an aluminum guide. The guide was machined to an outer diameter of 0.3175 inches, extending to a length of 1.25 inches followed by a 0.4 inch long taper at 15 degrees as shown in FIG. 5. The interior of the aluminum guide was drilled to an inner diameter of 0.1875 to properly fit the mount of the IR filament. The leads of the filament were attached to the wires using electrical shrink-wrap and wires were fed up through the inner hollow diameter of the tube.

The apparatus was placed in the tube (FIG. 6) and the wire leads were attached to a DC power supply (not shown). Approximately 4.5 volts at 0.74 amps was applied to the filament. Accordingly, the output wattage of the filament was approximately 3.4 Watts. At this wattage, the filament is designed to heat to about 800° C. This can be verified using an IR pyrometer. At these specifications, the tubes were heated for approximately 8 seconds. During the heating, the tubes were rotated constantly at approximately 1.25 revolutions per second with an electrical motor (not shown) to provide for even heating. After the prescribed period, the apparatus was quickly removed from the tube, and the beads were poured into the heated tube. After allowing the tube to harden for about 5-10 seconds, the tubes were inverted and excess beads were removed by banging the tube on a benchtop.

Example 8

Immobilization of protein A on polymer beads attached to the inner wall of microcentrifuge tubes. After bonding cyanogen bromide agarose beads to the wall of the microcentrifuge tube, the beads were treated according to manufacturer's instructions to attach protein A to the beads (see Instructions CNBr-activated Sepharose 4B, Amersham Biosciences, c. 2002, especially pp. 3-4; incorporated herein by reference). Briefly, the freeze-dried CNBr-activated agarose was swollen and washed with 1 mM HCl, and the protein A was dissolved in coupling buffer 1 M $NaHCO_3$, pH8.3, 0.5 M NaCl. The protein A was added to the bead coated tube and mixed end over end to allow binding. Excess protein A was washed away using coupling buffer. Any remaining active groups were blocked using Tris or ethanolamine.

Antibody binding was carried out in 1 ml wash buffer (20 mM $TrisPO_4$ buffer containing 1% Triton-X 100 and 250 mM NaCl) with approximately 35 µg Rabbit anti-rat antibody (ICN). Tubes were rotated end over end to allow binding. Tubes were washed 4-6 times with wash buffer. The antibody was eluted from the beads using Bradford reagent. Breadford reagent disrupts charge based interactions (i.e. protein A-antibody binding), but not covalent linkages (i.e. CNBr-protein A). The beads attached to the tube were found to bind 6.85 µg of protein A, whereas the free suspension beads (2 separate samples) were found to bind 18.93 and 17.98 µg of protein. Protein A agarose beads from CalbioChem (2 samples) were found to bind 15.46 and 18.30 µg of protein. These data demonstrate that the process of attaching the beads to the surface of the tube does not alter their ability to react with reagents commonly used with the beads.

Although an exemplary embodiment of the invention has been described above by way of example only, it will be understood by those skilled in the field that modifications may be made to the disclosed embodiment without departing from the scope of the invention, which is defined by the appended claims.

TABLE 1

Characteristics of the more common Ab immobilization procedures for use in AC

| Method of immobilization | Solid phase | Coupling procedure | Binding site of Ab | Ab direction |
|---|---|---|---|---|
| Physical adsorption | Carbon fabric | Incubation with Ab | Random | Random |
| Covalent attachment of intact Ab | Affi-Gel 10 (cross-linked agarose gel, carrying N-hydroxysuccinimide ester groups | Direct coupling with Ab | Random | Random |
| Attachment via Protein A | Sepharose-4B | Cross-linking of Ab to PrA-Sepharose with bifunctional reagent dimethylsuberimidate dihydrochloride | Amino groups of Fc region | Oriented |
| Attachment to metal-carrying media | Iminodiacetate resin | Loading of chelate resin with $CoCl_2$, attachment of Ab to resin and oxidation of cobalt ions to 3 + oxidation state by $H_2O_2$ | C-Terminal portion of Fc region | Oriented |
| Covalent attachment of oxidized Ab | Silica, activated with oxalic or adipic dihydrazide | Mixing of periodate-oxidized Ab with activated silica at pH 6 at 4° C. | Carbohydrate moieties of Fc hinge | Oriented |
| | Hydrazide-derivatized bead cellulose | Mixing of periodate-oxidized Ab with activated cellulose at pH 4 at 4° C. | Carbohydrate moieties of Fc hinge | Oriented |
| | Copolymer of 2-hydroxyethyl methacrylate and ethylene dimethacrylate, activated with 2,4,6-trichloro-1,3,5-triazine and modified with adipic acid dihydrazide | Mixing of periodate oxidized Ab with hydrazide-activated sorbent at pH 4 at 4° C. | Carbohydrate moieties of Fc hinge | Oriented |
| | Affi-Gel Hz (cross linked agarose gel with hydrazide groups) | Mixing of periodate-oxidized Ab with hydrazide-carrying sorbent at pH 4.8 at 4° C. | Carbohydrate moieties of Fc hinge | Oriented |
| | Bead cellulose, treated with 2,4,6-trichlorotriazine and activated with adipic acid dihydrazide | Mixing of periodate-oxidized Ab with cellulose hydrazide at pH 4.8 at 4° C. | Carbohydrate moieties of Fc hinge | Oriented |
| | Glass wool, treated with 3-aminopropyltriethoxysilane | Mixing of periodate-oxidized Ab with silanized glasswool at pH 5.5 at 4° C. and further treatment with sodium borohydride | Carbohydrate moieties of Fc hinge | Oriented |

TABLE 2

Reagents used for covalent non-oriented immobilization Ab

| Agents | Functional groups of Ab | Solid Phase |
|---|---|---|
| Soluble activators | | |
| N'-(3-dimethylaminopropyl) carbodiimide hydrochloride or N-ethyl-N'-(dimethylaminopropyl) carbodiimide hydrochloride | Amine groups | Carboxymethyl dextran; poliimide, activated by cyanogens bromide; gold surface, covered with w-mercaptohexadadeecanoic acid; cross-linked glycoprotein lattice |
| N-hydroxysuccinimide or sulfo-N-hydroxysucinimide | Amine groups | Carboxymethyl dextran; modified quartz fiber; gold surface, covered with w-mercaptohexadecanoic acid |
| Cyanogen bromide | Amine groups | Sepharose 4B |
| Thionyl chloride | Amine groups | Gold surface, vovered with w-mercaptohexadecanoic acid |
| p-Nitrophenol | Amine group | Gold surface, vovered with w-mercaptohexadecanoic acid |

TABLE 2-continued

Reagents used for covalent non-oriented immobilization Ab

| Agents | Functional groups of Ab | Solid Phase |
|---|---|---|
| Cyanuric chloride | Carboxylic groups | Gold surface, vovered with w-mercaptohexadecanoic acid |
| Phenylene diisocyanate | Carboxylic groups | Gold surface, vovered with w-mercaptohexadecanoic acid |
| Soluble bifunctional cross-linkers | | |
| Glutardialdehyde | Amine groups | Silanized quartz crystal; quartz surface, covered with poly (ethylenimide); silanized silicon nitride wafer |
| Benzophenone-4 isothiocyanate | | Aminopropylated silicon |
| 3-trifluorementhyl 3-(m-isothiocyanatOphenyl) diazirine | | Aminopropylated silicon |
| Solid phase bound activators | | |
| Oxirane compounds (epoxy derivatives) | Amino groups | Acrylic beads |
| N-hydroxysuccinimide ester groups | Amine groups | Affi-Gel 10 |
| Maleic anhydride groups | Amine groups | Nylon surface, covered with maleic anhydride/methylvinyl ether copolymer |

TABLE 3

Measurement of Ras Activation in Cultured Cells Using Protein A-Coated Glass Beads or Protein G-Agarose Beads

| | Proteinn A-Coated glass beads | | | Protein G-agarose beads | | |
|---|---|---|---|---|---|---|
| Cell line | GTP | GTP + GDP | % | GTP | GTP + GDP | % |
| | fmol/µg DNA | | | fmol/µg DNA | | |
| HL-60 | 4.3 ± 0.4 | 14.8 ± 1.6 | 29 | 0.9 ± 0.1 | 3.3 ± 0.4 | 26 |
| MB-231 | 2.1 ± 0.3 | 5.4 ± 0.4 | 39 | 1.0 ± 0.1 | 2.8 ± 0.3 | 36 |
| | fmol/mg protein | | | fmol/mg protein | | |
| NIH 3T3 | 5.2 ± 0.6 | 1031 ± 165 | 0.5 | 2.3 ± 0.2 | 328 ± 41 | 0.7 |

We claim:

1. A method for isolating a macromolecule, comprising:
   partially melting an inner wall of a test tube;
   contacting the partially melted inner wall of the test tube with a plurality of beads after partially melting the inner wall of the test tube;
   coating the beads with a capture reagent of the macromolecule; and
   incubating the coated beads with a solution containing the macromolecule under conditions to allow binding of the macromolecule to the capture reagent, thereby isolating the macromolecule.

2. The method of claim 1, wherein the beads are glass microbeads.

3. The method of claim 1, where in the beads are polymer microbeads.

4. The method of claim 3, wherein the microbeads are agarose.

5. The method of claim 1, wherein the capture reagent is attached to the beads by at least one linker molecule.

6. The method of claim 5, wherein the linker molecule is aminopropyltriethyoxysilane.

7. The method of claim 5, wherein the linker molecule is cyanogen bromide.

8. The method of claim 5, wherein in the linker molecule is a chemical cross-linking agent.

9. The method of claim 8, wherein the cross-linking agent is dimethyl suberimidate.

10. The method of claim 5, wherein the linker molecule is an antibody.

11. The method of claim 5, wherein the linker molecule is protein A or protein G.

12. The method of claim 1, further comprising washing the coated beads with the bound macromolecule with a wash buffer to remove unbound material while maintaining binding of the macromolecule to the capture reagent; and eluting the macromolecule from the capture reagent.

13. A method for isolating guanine nucleotide-binding proteins for determination of guanine nucleotide ratios comprising:
   partially melting an inner wall of a test tube;
   contacting the partially melted inner wall of the test tube with a plurality of glass beads wherein the beads have a surface after partially melting the inner wall of the test tube;
   reacting the beads with an agent to modify the surface of the beads to provide a plurality of free amino groups;
   reacting the free amino groups on the beads with a bifunctional amine cross-linker to provide a plurality of sites for binding a guanine nucleotide-binding protein binding partner; and
   incubating the coated beads with a solution containing the guanine nucleotide-binding protein under conditions to allow binding of the guanine nucleotide-binding protein to the binding partner while inhibiting nucleotide hydrolysis or release, thereby isolating the guanine nucleotide-binding protein.

14. A method comprising:
   heating a plurality of beads to a temperature sufficient to partially melt an inner wall of a tube;
   contacting the heated beads with the inner wall of the tube after heating the plurality of beads to the temperature sufficient to partially melt the inner wall of the tube;
   coating the beads with a capture reagent of a macromolecule; and
   incubating the coated beads with a solution containing the macromolecule under conditions to allow binding of the macromolecule to the capture reagent.

15. The method of claim 1, wherein the inner wall of the tube is partially melted using a heat gun.

16. The method of claim 1, wherein the inner wall of the tube is partially melted using infrared irradiation.

17. The method of claim 1, wherein the inner wall of the tube is partially melted using a filament.

18. The method of claim 1, wherein the tube is a microcentrifuge tube.

19. The method of claim 1, wherein the tube comprises a polymeric material, polypropylene, or polystyrene.

20. The method of claim 1, wherein the macromolecule is a protein, peptide, nucleic acid, carbohydrate, or polymer.

21. The method of claim 1, wherein the macromolecule is a polynucleotide.

22. The method as in claim 12, wherein the wash buffer is removed by inversion of the tube.

23. The method of claim 13, further comprising washing the coated beads with the bound guanine nucleotide-binding protein with a wash buffer to remove unbound material while maintaining binding of the guanine-nucleotide binding protein to the binding partner and inhibiting nucleotide hydrolysis and release; releasing the bound nucleotide from the guanine-nucleotide binding protein; and determining the ratio of guanine nucleotides released from the guanine nucleotide-binding proteins.

24. The method of claim 14, further comprising washing the coated beads with the bound macromolecule with a wash buffer to remove unbound material while maintaining binding of the macromolecule to the capture reagent; and eluting the macromolecule from the capture reagent.

* * * * *